US00PP27602P2

(12) United States Plant Patent
Roberts

(10) Patent No.: US PP27,602 P2
(45) Date of Patent: Jan. 24, 2017

(54) MINT PLANT 'OCHOCO MINT'

(50) Latin Name: ***Mentha* sp.**
Varietal Denomination: Ochoco Mint

(71) Applicant: Essex Laboratories, Inc., Napavine, WA (US)

(72) Inventor: Donald D. Roberts, Independence, OR (US)

(73) Assignee: Essex Laboratories, LLC, Chehalis, WA (US)

( * ) Notice: Subject to any disclaimer, the term of this patent is extended or adjusted under 35 U.S.C. 154(b) by 0 days.

(21) Appl. No.: 14/999,512

(22) Filed: May 18, 2016

(51) Int. Cl.
*A01H 5/12* (2006.01)

(52) U.S. Cl.
USPC ..... Plt./259

(58) Field of Classification Search
USPC ..... Plt./259
See application file for complete search history.

(56) References Cited

PUBLICATIONS

Hussain, Abdullah I., et al., "Seasonal variation in content, chemical composition and antimicrobial and cytotoxic activities of essential oils from four *Mentha* species," Journal of the Science of Food and Agriculture, 2010, 90(11), 1827-1836.

Mahmoud, Soheil S., et al., "Menthofuran regulates essential oil biosynthesis in peppermint by controlling a downstream monoterpene reductase," Proc. Natl. Acad. Sci, USA, Nov. 25, 2003; 100(24) 14481-8.

Rohloff, Jens, et al., "Effect of harvest time and drying method on biomass production, essential oil yield, and quality of peppermint (*Mentha piperita* L.)"; J. Agric. Food Chem., 2005, 53(10), pp. 4143-4148.

Rohloff, Jens, "Monoterpene composition of essential oil from peppermint (*Mentha piperita* L.) with regard to leaf position using solid-phase microextraction and gas chromatography/mass spectrometry analysis;" J. Agric. Food Chem.; 1999, 47(9), pp. 3782-3786.

Verma, R. S., et al., "Essential oil composition of menthol mint (*Mentha arvensis*) and peppermint (*Mentha piperita*) cultivars at different stages of plant growth from Kumaon Region of Western Himalaya," 2010, J. Medicinal and Aromatic Plants, vol. 1(1): 13-18.

*Primary Examiner* — Annette Para
(74) *Attorney, Agent, or Firm* — Marger Johnson

(57) ABSTRACT

Mint selection 14-41-16 denominated 'Ochoco Mint' is a new *Mentha* sp. cultivar that produces an essential oil different in composition than commercially grown mint varieties. The essential oil is similar to standard mint oil in components composition but differs in the typical ratio of components. Organoleptically, it differs from typical peppermint oil. It is resistant to mint rust and more resistant to *Verticillium* mint wilt than current commercially grown varieties of *M. arvensis*.

3 Drawing Sheets

Latin name of the genus and species: *Mentha* sp.
Variety denomination: 'OCHOCO MINT'.

TYPE OF PLANT AND NAME OF VARIETY

The present invention relates to a new and distinct variety of peppermint plant developed from a parent of the species *Mentha arvensis*. The new variety will be identified as 'Ochoco Mint'.

BACKGROUND OF INVENTION

Selection 'Ochoco Mint' originated as a seedling from an open pollinated mint plant (12-5-11) that originated from a *M. arvensis* parent line. The parent to 'Ochoco Mint' was one of several mint lines in a polycross breeding system composed of selected male and female fertile genotypes.

DISCOVERY AND ASEXUAL REPRODUCTION

This new peppermint was developed in a mint breeding program in which the primary objective was to develop a Mitcham type peppermint variety having a specific oil composition, acceptable yield and resistant to diseases mint wilt and mint rust. Mint wilt is caused by a soil-borne fungus, *Verticillium dahliae* and mint rust is a leaf infection caused by the air-borne fungus *Puccinia menthae*. Only seedlings with no symptoms of mint wilt or rust were selected from the progeny population for further evaluation. Selection 'Ochoco Mint' was vegetatively propagated from original seedling to increase it to 20 plants for continued evaluation in 2014. The selection was again vegetatively propagated to over 300 plants for planting and evaluation in 2015. When compared to Black Mitcham as a control, 'Ochoco Mint' had less or no symptoms of mint wilt than the control and had no mint rust infection. Oil yield of 'Ochoco Mint' is better than 'Black Mitcham' in test plots as a single plant and as multiple plants in larger plots.

Selection 'Ochoco Mint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. Under the inventor's direction, Premier Botanicals has conducted asexual propagation of 'Ochoco Mint' for greenhouse and field planting in Monmouth, Oreg., each year since 2014 and the genotype comes true to form with each generation.

SUMMARY OF THE INVENTION

Mint selection 14-41-16, denominated 'Ochoco Mint' is a new *Mentha* sp. cultivar that produces an essential oil different in composition than commercially grown mint varieties. The essential oil is similar to standard mint oil in components composition but differs in the typical ratio of components. Organoleptically, it differs from typical peppermint oil. It is resistant to mint rust (*Puccinia menthae*) and mint wilt (*Verticillium dahlia*).

BRIEF DESCRIPTION OF THE FIGURES

The accompanying color figures show typical greenhouse (FIG. 1) and field grown vegetative growth (FIG. 3) of 14-41-16 denominated 'Ochoco Mint' and depicts the color as nearly true as reasonably possible.

FIG. 1 illustrates the flowering pattern and multiple flowering shoots of my new mint plant in accordance with the present invention.

FIG. 2 illustrates the leaf shape and the flower spike with capitate flower development at the nodes of the spike.

FIG. 3 illustrates the growth pattern under field management of my new mint plant in accordance with the present invention.

DESCRIPTION OF PLANT

My new mint plant improves upon and is distinct from other mint plants in several characteristics, including but not limited to, the following:

1. The ability to produce an essential oil different in composition but with similar components as 'Black Mitcham' peppermint;
2. A branching pattern similar to its parent and an upright growth to facilitate harvest;
3. An early spring growth similar to *M. piperita* but with an earlier maturity for desirable chemical composition of its essential oil;
4. A level of resistance to mint wilt (*Verticillium dahliae*) equal to or greater than that of its parent;
5. Resistance to mint rust caused by *Puccinia menthae*.

The essential oil extracted from 'Ochoco Mint' has the same components as that of commercial oil produced by 'Black Mitcham' peppermint and the parent 12-5-11 as illustrated in Table 1. However, the ratio of oil components differs between the parent line and commercial peppermint oil and that of 'Ochoco Mint'. The concentration of menthone and menthol in the oil of 'Ochoco Mint' is lower than that of 'Black Mitcham'. The amount of menthofuran in the oil of 'Ochoco Mint' is higher than that of 'Black Mitcham', but lower than the parent. Organoleptically, the oil of 'Ochoco Mint' is different from that of 'Black Mitcham' and *M. arvensis*, reflecting the difference in oil component ratios.

TABLE 1

A Comparison of 'Ochoco Mint' Essential Oil collected from test plots near Monmouth, Oregon, to that of commercial 'Black Mitcham' Peppermint Oil, from Parent Line 12-5-11, and *M. arvensis*.

| Essential Oil Components | Commercial Black Mitcham 1/ | 'Blanco' *M. arvensis* 2/ | 12-5-11 Parent Seedling 3/ | 'Ochoco Mint' 4/ |
|---|---|---|---|---|
| 1-Limonene | 1.7 | 3.0 | 1.8 | 3.5 |
| 1,8-Cineole | 4.9 | <1.0 | 9.7 | 6.1 |
| 1-Menthone | 19.4 | 7.3 | 3.8 | 8.7 |
| Menthofuran | 4.2 | 0.0 | 37.1 | 18.2 |

TABLE 1-continued

A Comparison of 'Ochoco Mint' Essential Oil collected from test plots near Monmouth, Oregon, to that of commercial 'Black Mitcham' Peppermint Oil, from Parent Line 12-5-11, and *M. arvensis*.

| Essential Oil Components | Commercial Black Mitcham 1/ | 'Blanco' *M. arvensis* 2/ | 12-5-11 Parent Seedling 3/ | 'Ochoco Mint' 4/ |
|---|---|---|---|---|
| Isomenthone | 3.1 | 3.6 | 1.2 | 0.7 |
| 1-Menthyl Acetate | 5.3 | 2.9 | 6.0 | 7.1 |
| 1-Menthol | 44.6 | 73.9 | 26.8 | 38.6 |
| Pulegone | 2.1 | 0.0 | 4.3 | 1.1 |

The numbers listed in the above table are percentages based upon the analysis of the respective mint oils by gas chromatograph. The percentages are determined by calculation of the relative peak areas.

1/ Black Mitcham oil sample typical of what is produced commercially.

2/ Commercial oil sample typical of what is produced by *Mentha arvensis*.

3/ Parent line 12-5-11 oil from plants harvested from research test plots.

4/ 'Ochoco Mint' oil from plants harvested from research plots.

TAXONOMIC DESCRIPTION OF 'OCHOCO MINT'

This new plant, under greenhouse and field growing conditions, is a bush type plant with lateral branches at each node of the main stems. The height of 'Ochoco Mint' is slightly less than Black Mitcham growing under similar conditions and will vary based on fertilizer, soil quality, and water application, amongst other known factors that affect growth patterns. Secondary and tertiary branching occurs to form a compact growth habit. When 'Ochoco Mint' is mature and ready for harvest, the main stem at mid-plant (approximately between the eleventh and twelfth node) is 6-7 mm in width. The secondary branch stems are 3-5 mm.

Mature leaves at the bottom of the plant are ovate lanceolate as are leaves on secondary branch stems. Leaves on upper mature plants, both main and secondary stems, are more lanceolate (FIG. 3). Mid-main stem leaf size at flowering is 35-40 mm in width and 40-50 mm in length. Leaf size on secondary branches at flowering is 11-15 mm in width and 40-50 mm in length. Leaf petioles on the main stem leaves are 8-10 mm in length while petioles on secondary branch stem leaves are 8-10 mm in length. Leaves on the mid-main stem and lower tend to be slightly lobed and denticulate while the leaves on the upper plant tend to be more dentate. The main stem leaves have from 14 to 16 teeth on each side. The leaf is dark green in color, ranging from The Fifth Edition Royal Horticultural Society Colour Chart 137B to 137C in the green group classification. The leaf has 6-9 lateral veins, more or less in parallel off the main vein that runs from the petiole to the tip of the leaf. The veins are prominent in all leaves of 'Ochoco Mint'.

The inflorescence is an inconspicuous spike with capitate flowers developing at the last few nodes of the stem. The capitate flowers are 18-22 mm in width and 10-12 mm in length. The flowers consist of five petals fused into a two lipped corolla. The corolla is violet in color ranging from The Fifth Edition Royal Horticultural Society Colour Chart 85C to 85D in the violet group. The calyx is generally yellow-green and is 144B in The Fifth Edition Royal Horticultural Society Colour Chart, yellow-green group. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust and mint wilt, and producing a unique essential oil.

* * * * *

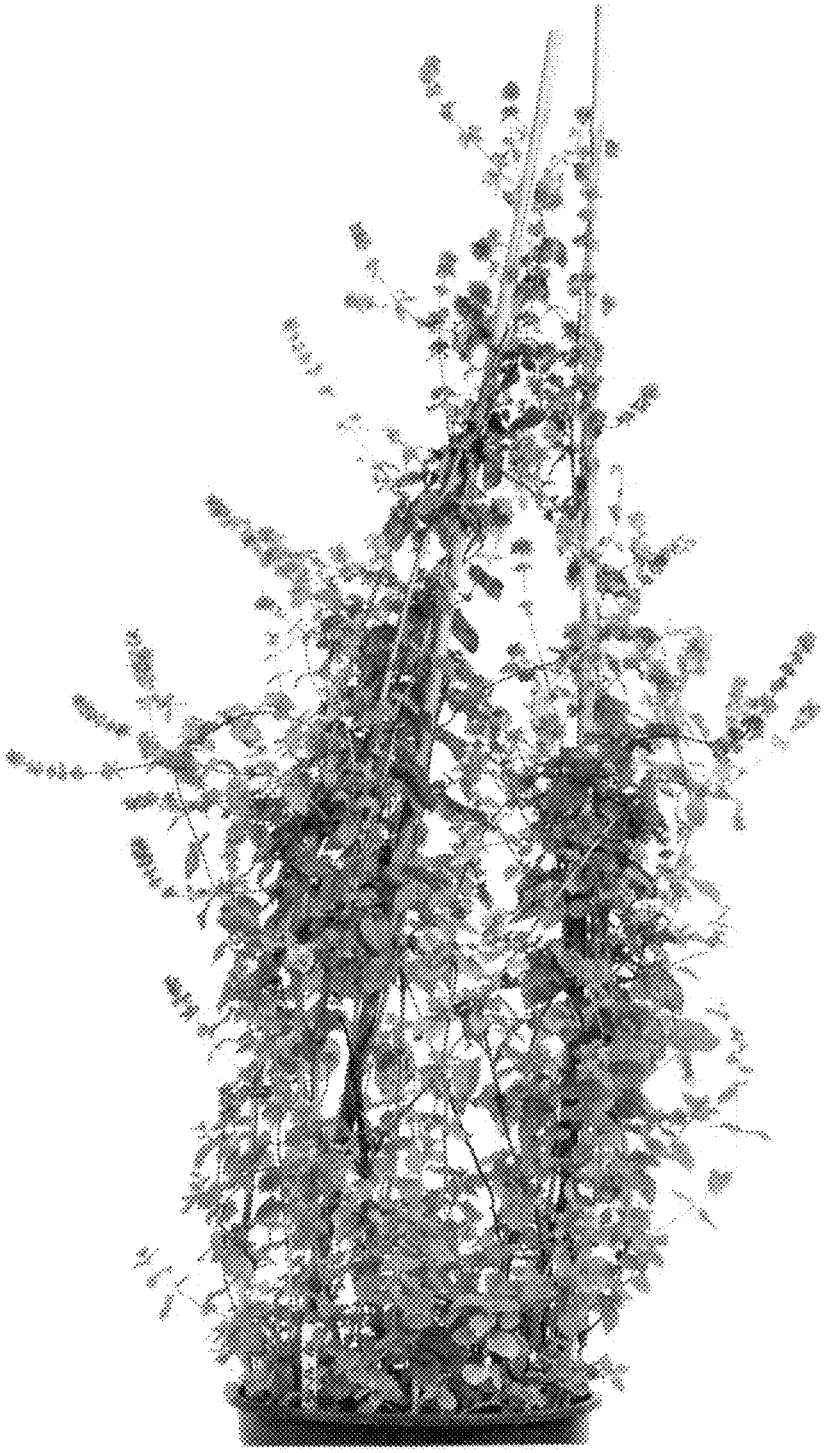
14 - 41 - 16

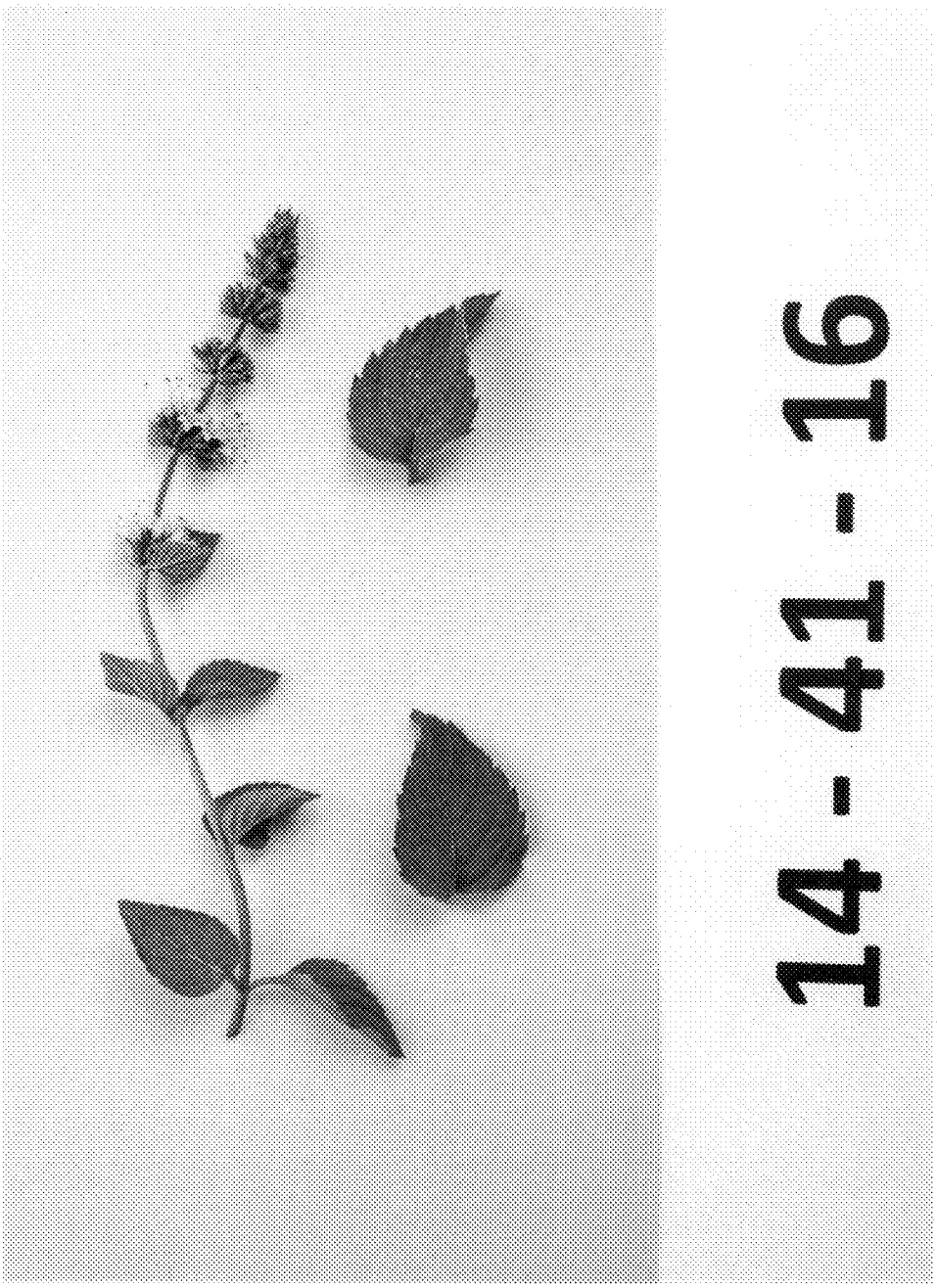
14 - 41 - 16

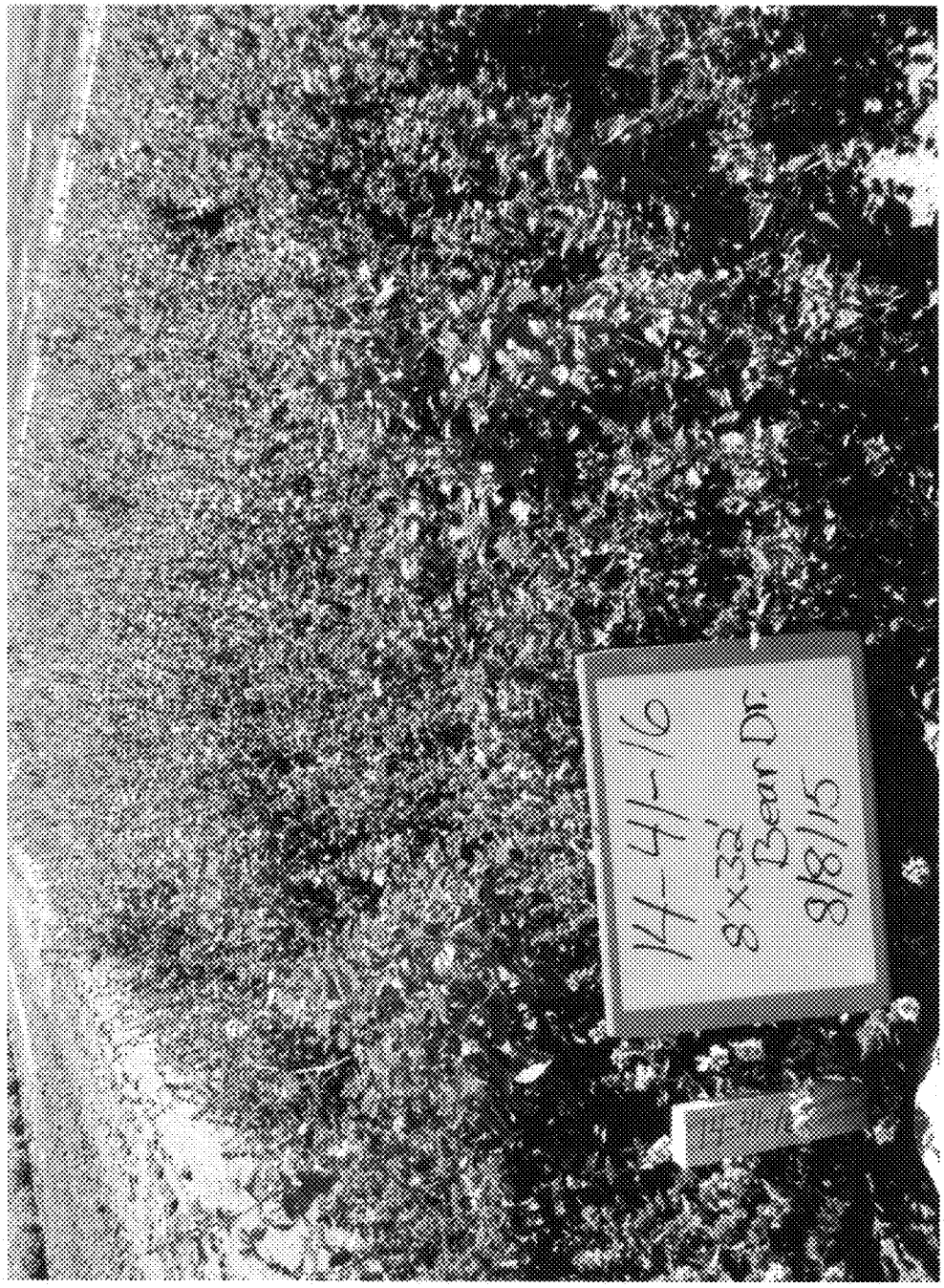
14-14-16
8x8
Bear Dr
5/18/16